United States Patent [19]

Gallati et al.

[11] 4,206,280

[45] Jun. 3, 1980

[54] DETERMINATION OF ACID PHOSPHATASE

[75] Inventors: Harald Gallati, Arlesheim; Marc Roth, Geneva, both of Switzerland

[73] Assignee: Hoffmann-La Roche Inc., Nutley, N.J.

[21] Appl. No.: 959,128

[22] Filed: Nov. 9, 1978

Related U.S. Application Data

[63] Continuation of Ser. No. 747,652, Dec. 6, 1976, abandoned.

[30] Foreign Application Priority Data

Dec. 25, 1975 [CH] Switzerland .................. 16779/75

[51] Int. Cl.$^2$ ............................................. C12Q 1/42
[52] U.S. Cl. ................................... 435/21; 252/408
[58] Field of Search ............. 435/21, 196; 252/408 R

[56] References Cited

U.S. PATENT DOCUMENTS

| | | | |
|---|---|---|---|
| 3,331,857 | 7/1967 | Coleman | 260/343.4 |
| 3,425,912 | 2/1969 | Deutsch | 435/21 |
| 3,595,756 | 2/1971 | Stecin | 435/21 |
| 3,799,843 | 3/1974 | Stravropoulos et al. | 435/21 |
| 3,823,071 | 7/1974 | Roy et al. | 435/21 |
| 4,045,290 | 8/1977 | Bulbenko et al. | 435/21 |

FOREIGN PATENT DOCUMENTS

| | | |
|---|---|---|
| 2059278 | 7/1971 | Fed. Rep. of Germany . |
| 2115748 | 10/1972 | Fed. Rep. of Germany . |
| 2120776 | 8/1972 | France . |

OTHER PUBLICATIONS

Bergmeyer, *Methods of Enzymatic Analysis*, vol. 2, Academic Press, New York, (1974), pp. 856–860.

Appleyard, "The Effect of Alcohols on the Hydrolysis of Sodium Phenolphthalein Diphosphate by Prostatic Effects", *Biochem J.* vol. 42, (1948), pp. 596–597.

Appleyard, "The Effect of Alcohols on the Hydrolysis of Sodium Phenolphthalein Diphosphate by Prostatic Effects", *Chem. Abstracts*, vol. 42, No. 22, (1948).

Ellis, et al., "Colorimetric Determination of Serum Acid Phosphatase Activity Using Adenosine 3'-monophosphate As Substrate", *Chem. Abstracts*, vol. 76, No. 13, (1972).

Wilkinson, *The Principles and Practice of Diagnostic Enzymology*, Yearbook Medical Publishers, Inc., Chicago, (1976), pp. 141–144.

*Primary Examiner*—Thomas G. Wiseman
*Attorney, Agent, or Firm*—Jon S. Saxe; George M. Gould; R. Hain Swope

[57] ABSTRACT

A method of improving the determination of acid phosphatase by adding a reagent which considerably increases the activity of the enzyme is disclosed. Also disclosed are reagent kits containing said reagent.

12 Claims, No Drawings

DETERMINATION OF ACID PHOSPHATASE

This is a continuation of application Ser. No. 747,652 filed Dec. 6, 1976, abandoned.

BACKGROUND OF THE INVENTION

Acid phosphatase, an enzyme which optimally splits phospho-monoesters under acidic conditions, is found in various organs in the human body, e.g. the prostate gland, liver and spleen and in blood cells. When tissue cells are damaged, acid phosphatase is transferred to the plasma. Therefore, the determination of acid phosphatase in body fluids, particularly serum or plasma, is a vluable tool in the diagnosis of diseases of the organs where it is normally found. For example, determination of significant levels of prostatic acid phosphatase in the serum of plasma is an indication of possible hypertrophy of the prostate gland or a carcinoma therein.

Determinations of the acid phosphatase activity in body fluids can present some difficulties since the activity of the enzyme is relatively low. It can therefore be appreciated that increasing the degree of activity of any given quantity of enzyme can be of considerable value in diagnostic procedures for its determination. In accordance with the present invention, it has been found that the addition of a straight-chain alcohol of 4-6 carbon atoms to the body fluid being tested, markedly increases the activity of acid phosphatase contained therein thus improving diagnostic determinations thereof.

BRIEF DESCRIPTION OF THE INVENTION

The present invention relates to an improved method for the determination of acid phosphatase in body fluids wherein the activity of the acid phosphatase present is increased by the addition to the fluid sample to be tested of one or more straight-chain alcohol containing from 4-6 carbon atoms.

DETAILED DESCRIPTION OF THE INVENTION

The improved method of determining acid phosphatase of human origin in body fluids comprises the addition to a test solution of an activator for acid phosphatase activity comprising one or more straight-chain alcohols containing from 4-6 carbon atoms. More particularly, the method of the present invention comprises adding to a sample of body fluid to be tested for acid phosphatase activity a solution containing from about 50 micromols to about 50 mmols, preferably from about 60 micromols to about 25 mmols per liter of a phospho-monoester substrate, from about 50 mmols to about 300 mmols, preferably about 100 mmols per liter of a buffer to adjust the pH to between about 4.5 and about 6.5, preferably between about 5 and about 6 and from about 10 mmols to about 300 mmols, preferably from about 100 mmols to about 200 mmols, per liter of the herein described activator, incubating the mixture at between about 20° C. and about 45° C. and measuring the action of the enzyme on the substrate.

The phospho-monoester substrates utilized in the method of the invention are recognized in the art and may be represented by the general formula:

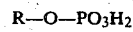

$$R\text{—}O\text{—}PO_3H_2$$

wherein R represents an organic indicator radical.

R in the above formula preferably represents a chromophoric radical such as, for example, 4-nitrophenyl, thymolphthalein, phenolphthalein, 2-chloro-4-nitrophenyl group or the like, or a fluorophoric group such as, for example, 1-naphthyl and the like. R may also represent other groups which may function as indicators such as, for example, adenosine, glycerine or phenyl.

The particular substrate utilized in determining acid phosphatase concentration in accordance with the invention is preferably utilized at optimum concentration. Such concentrations will vary with each substrate and will also vary somewhat with the ph value. Optimum substrate concentration at a given pH can be determined from a substrate activity curve which can be obtained by measuring the enzyme activity at various substrate concentrations under otherwise identical conditions. Thus, for example, at pH 5.5 the optimum concentration is about 25 mmols/liter for betaglycerine phosphate, 2.5 mmols/liter for 4-nitrophenyl phosphate and 100 mmols/liter for phenolphthalein diphosphate.

Suitable buffers utilized in acid phosphatase determinations in accordance with the present invention include, for example, citrate buffer, acetate buffer and the like.

The activators utilized in accordance with the present invention to enhance the activity of acid phosphatase are straight-chain alcohols containing 4-6 carbon atoms, preferably n-butanol, n-pentanol and 1,5-pentanediol. 1-Pentanol and 2-pentanol are particularly preferred. Although it is within the scope of the invention to utilize two or more of these activators, it is preferred to use them individually.

It is to be understood that the term "activator" as utilized in the context of the present invention is not intended to mean a substance which, per use, will cleave the substrate thereby causing a positive test. Further, the above-named straight-chain alcohols neither split the phospho-monoester substrate nor directly potentiate the activity of acid phosphatase. Instead, the fact that the phosphate groups split from the substrate by the enzyme are transferred to the activator acts to increase the activity of the enzyme.

In accordance with the present invention, a sample of the body fluid to be tested is mixed with an aqueous solution containing the substrate, activator and buffer and the mixture is incubated at from 20° C. to about 40° C., preferably between 30° C. and 37° C. The incubation period is generally from 5 to about 60 minutes, preferably about 30 minutes. The enzymatic reaction is then quenched by the addition of a solution containing a suitable base, such as, for example, sodium hydroxide, trisodium phosphate and the like and the substrate conversion measured.

The substrate conversion is a measure of the activity of the enzyme. The measurement can be of the decrease in the phospho-monoester concentration of the increase in the concentration of organic indicator group liberated. It is to be noted that, since the activation of the enzyme is effected by a transphosphorylation reaction, i.e. a phosphate transfer from the phospho-monoester to the activator, the amount of free phosphate in the reaction mixture after incubation does not correlate with substrate conversion and therefore cannot be utilized as indicator of enzyme activity.

The type of measurement utilized depends on the substrate selected. For example, photometric or fluorimetric measurements are utilized with 4-nitro-phenyl phosphate, thymolphthalein phosphate, phenolphthalein phosphate or naphthyl phosphate as the substrate.

Certain other substrates such as, for example, betaglycerine phosphate, phenyl phosphate or adenosine monophosphate require that the organic indictor group liberated by the action of acid phosphatase be converted into a substance the concentration of which can be determined photometrically. For example, if phenyl phosphate is used as the substrate, the phenol liberated is converted into a blue dyestuff using a phenol reagent, e.g. FolinCiocalteus, Merck 9001 and the like. Also, the enzymatic reaction can be measured kinetically utilizing compounds such as, for example, 2-chloro-4-nitrophenyl phosphate as the substrate.

The method of the present invention is suitable for both manual and automatic determinations of acid phosphatase. The method can be carried out on serum, plasma, blood, fluid and urine.

The reagents utilized in the improved method of the present invention are preferably packaged in a reagent kit. A typical kit would contain, in one or more containers, the phospho-monoester, the buffer and the activator. Additives conventionally included in diagnostic preparations such as, for example, detergents such as polyoxyethylene lauryl ether and the like, stabilizers and the like may also be included. Such substances may be added to any of the components of the kit. The reagents may be separate or, where appropriate, may be combined, e.g. the buffer and the activator may be packaged as a single solution. The reagent kits may additionally contain other components useful in the acid phosphatase determination such as, for example, a control or standard solution, a reagent for quenching the reaction and/or a reagent for conversion of the organic radical liberated, where applicable. The aforementioned additive materials may also be included in a separate container, if desired. With the exception of the activator which is a liquid, the various reagents, control solutions and the like may be in liquid or in solid form, e.g. as powders, granules, tablets or in a lyophilized form.

The following examples illustrate the present invention. All temperatures are given in degrees Centigrade.

EXAMPLE 1

A sample of 0.1 ml of acid prostate gland phosphatase solution (isolated by the method described by Lam et al., Clin. Chem. 19 483, 1973) was mixed with 2.0 ml of a substrate-buffer solution containing 0.1 mol/liter of citrate buffer (pH 5.25), 5 g/liter of Brij-35 (polyoxyethylene lauryl ether), 5 mmols/liter of 4-nitro-phenyl phosphate and various concentrations of 1-pentanol as given below. Each mixture was incubated at 37° for 30 minutes. The reaction was stopped by adding 1.0 ml of 1—N sodium hydroxide solution and the 4-nitro-phenolate liberated was determined photometrically at a wave-length of 405 nm.

The results are given in Table I in terms of the percent prostate gland phosphatase activity for various concentrations of 1-pentanol in comparison to a control solution which contained no 1-pentanol.

Table I

| 1-Pentanol Concentration (mmols/liter) | Activity of Prostate Gland Phosphatase |
|---|---|
| Control | 100% |
| 50 | 127% |
| 100 | 173% |
| 150 | 189% |
| 200 | 139% |

EXAMPLE 2

The method described in Example 1 was repeated utilizing 2-pentanol as the activator. The results are given in Table II.

Table II

| 2-Pentanol Concentration (mmols/liter) | Activity of Prostate Gland Phosphatase |
|---|---|
| Control | 100% |
| 50 | 138% |
| 100 | 172% |
| 150 | 190% |
| 200 | 139% |

EXAMPLE 3

The method described in Example 1 was repeated utilizing 1,5-pentanediol as the activator. The results are given in Table III.

Table III

| 1,5-Pentanediol Concentration (mmols/liter) | Activity of Prostate Gland Phosphatase |
|---|---|
| Control | 100% |
| 50 | 120% |
| 100 | 131% |
| 150 | 140% |
| 200 | 148% |

EXAMPLE 4

The method described in Example 1 was repeated utilizing 1-butanol as the activator. The results are given in Table IV.

Table IV

| 1-Butanol Concentration (mmols/liter) | Activity of Prostrate Gland Phosphatase |
|---|---|
| Control | 100% |
| 50 | 119% |
| 100 | 131% |
| 150 | 131% |
| 200 | 116% |

EXAMPLE 5

The method described in Example 1 was repeated utilizing 1-hexanol as the activator. The results are given in Table V.

Table V

| 1-Hexanol Concentration (mmols/liter) | Activity of Prostate Gland Phosphatase |
|---|---|
| Control | 100% |
| 25 | 107% |
| 50 | 114% |
| 100 | 120% |

EXAMPLE 6

A sample of 0.05 ml of prostate gland phosphatase solution was mixed with 2.0 ml of a substrate-buffer solution containing 0.1 mol/liter of acetate buffer (pH 5.5), 62 micromols/liter of phenolphthalein diphosphate and various concentrations of 1-pentanol as given below. The mixture was incubated at 37° for 15 minutes. In order to stop the reaction and to develop the color, 2.0 ml of 0.4 mol/liter sodium phosphate buffer (pH 10) was added to the solution. The color intensity was measured at a wave-length of 546 nm.

The results are given in Table VI in terms of the percent prostate gland phosphatase activity for various concentrations of 1-pentanol in comparison to a control solution which contained no 1-pentanol.

Table VI

| 1-Pentanol Concentration (mmols/liter) | Activity of Prostate Gland Phosphatase |
| --- | --- |
| Control | 100% |
| 50 | 154% |
| 100 | 174% |
| 150 | 177% |
| 200 | 131% |

EXAMPLE 7

A sample of 0.1 ml of erythrocyte phosphatase was mixed with 2.0 ml of a substrate-buffer solution containing 0.1 mol/liter of acetate buffer (pH 5.5), 5 mmols/liter of 4-nitrophenyl phosphate, 5 g/liter of Brij-35 (polyoxyethylene lauryl ether) and various concentrations of 1-pentanol. After 30 minutes incubation at 37°, the reaction was stopped by the addition of 1.0 ml of 1-N sodium hydroxide solution and the 4-nitrophenolate liberated was determined photometrically at a wave-length of 405 nm.

Table VIII

| 1-Pentanol Concentration (mmols/liter) | Activity of Erythrocyte Phosphatase |
| --- | --- |
| Control | 100% |
| 50 | 132% |
| 100 | 153% |
| 150 | 162% |
| 200 | 136% |

EXAMPLE 8

Samples of 0.1 ml of serum were mixed with 0.5 ml of a substrate-buffer solution containing 0.1 mol/liter of citrate buffer (pH 5.5) and 5 mmols/liter of 4-nitrophenyl phosphate. After 30 minutes incubation at 37°, the reaction was stopped by the addition of 2.5 ml of 0.1-N sodium hydroxide solution and the 4-nitrophenolate liberated was determined photometrically at a wave-length of 405 nm. The determination of the activity of acid phosphatase was carried out in the absence of 1-pentanol (control) and in the presence of 150 mmols/liter of 1-pentanol for each sample of serum.

The results are given in Table VIII.

Table VIII

| Serum Sample No. | Activity without 1-pentanol (units/liter) | Activity with 150 mmols/liter of 1-pentanol (units/liter) |
| --- | --- | --- |
| 1 | 1.12 | 2.10 |
| 2 | 16.63 | 24.55 |
| 3 | 18.41 | 31.53 |
| 4 | 20.65 | 33.59 |

EXAMPLE 9

A sample of 0.1 ml of prostate gland phosphatase solution was mixed with 2.0 ml of a substrate-buffer solution containing 0.1 mol/liter of acetate buffer (pH 5.5) and various concentrations of phenyl phosphate. After 5 minutes incubation at 37°, 0.5 ml of phenol reagent [Folin-Ciocalteus] and 1.0 ml of 20% sodium carbonate solution were pipetted in and the mixture incubated for a further 10 minutes at 37°. The intensity of the blue dye, which corresponds to the concentration of phenol liberated, was measured at a wave-length of 578 nm. These determinations were carried out in the absence of 1-pentanol (control) and in the presence of 150 mmols/liter of 1-pentanol for each concentration of phenyl phosphate.

The results are given in Table IX.

Table IX

| Phenyl Phosphate Concentration in Test Solution (mmols/liter) | Difference in Photometric Reading For Five Minute Incubation | |
| --- | --- | --- |
| | Without 1-Pentanol | 1-Pentanol, 150 mmols/liter |
| 0.078 | 0.105 | 0.169 |
| 0.155 | 0.150 | 0.280 |
| 0.312 | 0.198 | 0.390 |
| 0.625 | 0.245 | 0.490 |
| 1.25 | 0.275 | 0.550 |
| 2.50 | 0.280 | 0.590 |
| 5.00 | 0.280 | 0.590 |

EXAMPLE 10

A 0.05 ml sample of purified prostate gland phosphatase solution was mixed with 1.0 ml of a substrate-buffer solution containing 0.1 mol/liter acetate buffer (pH 5.5), 0.5 mmol/liter phenolphthalein monophosphate and various concentrations of 1-pentanol. After 10 minutes incubation at 37°, the reaction was stopped by adding 2.0 ml of a 0.4 mol/liter sodium phosphate buffer solution (pH 10). The phenolphthalein liberated was determined photometrically at a wave-length of 546 nm.

The results are given in Table X in terms of percent prostate gland phosphatase activity for various concentrations of 1-pentanol in comparison to a control solution which contained no 1-pentanol.

Table X

| 1-Pentanol Concentration (mmols/liter) | Activity of Prostate Gland Phosphatase |
| --- | --- |
| Control | 100% |
| 50 | 125% |
| 100 | 135% |
| 150 | 140% |

EXAMPLE 11

A 0.05 ml sample of purified prostate gland phosphatase solution was mixed with 1.0 ml of a substrate-buffer solution containing 0.1 mol/liter citrate buffer (pH 5.75), 1.2 mmols/liter thymolphthalein phosphate, 5 g/liter of Brij-35 (polyoxyethylene lauryl ether) and various concentrations of 1-pentanol. After 10 minutes incubation at 37°, the reaction was stopped by adding 2.0 ml of a 0.2 mol/liter bicarbonate buffer solution (pH 10). The thymolphthalein liberated was determined photometrically at a wave-length of 578 nm.

The results are given in Table XI in terms of the percent prostate gland phosphatase activity for various concentrations of 1-pentanol in comparison to a control solution which contained no 1-pentanol.

Table XI

| 1-Pentanol Concentration (mmols/liter) | Activity of Prostate Gland Phosphatase |
| --- | --- |
| Control | 100% |
| 50 | 117% |
| 100 | 125% |

Table XI-continued

| 1-Pentanol Concentration (mmols/liter) | Activity of Prostate Gland Phosphatase |
|---|---|
| 150 | 140% |

We claim:

1. In a method of determining acid phosphatase activity in a sample of body fluid comprising the steps of mixing with said sample predetermined quantities of a phospho-monoester substrate having an organic indicator radical and a suitable buffer to adjust the pH to between about 4.5 and 6.5, incubating said mixture for a predetermined period, stopping said incubation and measuring the substrate conversion, the improvement which comprises adding to said mixture prior to incubation an activator for acid phosphatase activity consisting of one or more straight-chain aliphatic alcohols containing from 4 to 6 carbon atoms having a conventration from about 10 mmols to about 300 mmols per liter.

2. A method in accordance with claim 1 wherein and said substrate is present in said mixture at a concentration of between about 50 micromoles and about 50 mmols per liter, and said buffer is present in from about 50 mmols to about 300 mmols per liter.

3. A method in accordance with claim 1 wherein said substrate is present in said mixture at a concentration of between about 60 micromoles and about 25 mmols per liter, said buffer is present in about 100 mmols per liter and a sufficient amount of said activator is added to achieve a concentration of from about 100 mmols to about 200 mmols per liter.

4. The method in accordance with claim 1 wherein said activator is n-butanol.

5. The method in accordance with claim 1 wherein said activator is 1-pentanol.

6. The method in accordance with claim 1 wherein said activator is 2-pentanol.

7. The method in accordance with claim 1 wherein said activator is 1,5-pentanediol.

8. In a reagent kit suitable for the determination of acid phosphatase in body fluid, said kit comprising, in one or more containers:
   (a) a phospho-monoester substrate having an organic indicator radical; and
   (b) a suitable buffer to adjust the pH of a test sample to between about 4.5 and 6.5,
the improvement which comprises also providing in said kit an activator for acid phosphatase activity consisting of one or more straight-chain aliphatic alcohols containing from 4 to 6 carbon atoms having a composition of 10 mmols to 300 mmols per liter.

9. A reagent kit in accordance with claim 8 wherein said activator is n-butanol.

10. A reagent kit in accordance with claim 8 wherein said activator is 1-pentanol.

11. A reagent kit in accordance with claim 8 wherein said activator is 2-pentanol.

12. A reagent kit in accordance with claim 8 wherein said activator is 1,5 pentanediol.

* * * * *